(12) United States Patent
Schweizer

(10) Patent No.: US 10,364,729 B2
(45) Date of Patent: Jul. 30, 2019

(54) DETERMINING AN AMMONIA MASS FLOW BETWEEN TWO SCR CATALYTIC CONVERTERS

(71) Applicant: Robert Bosch GmbH, Stuttgart (DE)

(72) Inventor: Frank Schweizer, Schwaikheim (DE)

(73) Assignee: Robert Bosch GmbH, Stuttgart (DE)

( * ) Notice: Subject to any disclaimer, the term of this patent is extended or adjusted under 35 U.S.C. 154(b) by 157 days.

(21) Appl. No.: 15/417,366

(22) Filed: Jan. 27, 2017

(65) Prior Publication Data
US 2017/0218828 A1 Aug. 3, 2017

(30) Foreign Application Priority Data
Feb. 3, 2016 (DE) .................. 10 2016 201 602

(51) Int. Cl.
| | |
|---|---|
| *G01M 15/10* | (2006.01) |
| *F01N 11/00* | (2006.01) |
| *F01N 13/00* | (2010.01) |
| *B01D 53/94* | (2006.01) |
| *F01N 3/20* | (2006.01) |
| *G01F 1/78* | (2006.01) |
| *G01N 11/02* | (2006.01) |
| *F01N 9/00* | (2006.01) |

(52) U.S. Cl.
CPC .......... *F01N 11/00* (2013.01); *B01D 53/9418* (2013.01); *B01D 53/9495* (2013.01); *F01N 3/208* (2013.01); *F01N 9/00* (2013.01); *F01N 13/009* (2014.06); *G01F 1/78* (2013.01); *G01N 11/02* (2013.01); *B01D 2251/2062* (2013.01); *F01N 2550/05* (2013.01); *F01N 2610/02* (2013.01); *F01N 2900/0402* (2013.01); *F01N 2900/1616* (2013.01); *F01N 2900/1824* (2013.01); *Y02T 10/47* (2013.01)

(58) Field of Classification Search
USPC .............................. 73/114.69, 114.71, 114.75
See application file for complete search history.

(56) References Cited

U.S. PATENT DOCUMENTS

| | | | |
|---|---|---|---|
| 2008/0022655 A1* | 1/2008 | Forthmann | F01N 3/0234 60/274 |
| 2010/0024401 A1* | 2/2010 | Ichikawa | F01N 3/2066 60/286 |
| 2010/0242454 A1 | 9/2010 | Holderbaum | |
| 2011/0011152 A1* | 1/2011 | Ito | G01N 27/4074 73/23.31 |

(Continued)

FOREIGN PATENT DOCUMENTS

| | | |
|---|---|---|
| DE | 102013203579 A1 | 9/2014 |
| EP | 2787186 A1 | 10/2014 |

*Primary Examiner* — Eric S. McCall
(74) *Attorney, Agent, or Firm* — Michael Best & Friedrich LLP

(57) ABSTRACT

A method for determining a mass flow of ammonia between two SCR catalytic converters disposed one after the other in an SCR catalytic converter system in an exhaust system, which comprises only one reduction agent dosing unit upstream of the first SCR catalytic converter, characterized in that the determination is carried out from the signal of a NOx sensor disposed between the two SCR catalytic converters and the signal of a NOx sensor disposed downstream of the second SCR catalytic converter.

10 Claims, 2 Drawing Sheets

(56) References Cited

U.S. PATENT DOCUMENTS

| | | | |
|---|---|---|---|
| 2011/0023591 A1* | 2/2011 | Dobson | F01N 3/106 |
| | | | 73/114.75 |
| 2012/0144801 A1* | 6/2012 | Levijoki | F01N 3/208 |
| | | | 60/274 |
| 2012/0180558 A1* | 7/2012 | Li | G01M 15/102 |
| | | | 73/114.75 |
| 2013/0298655 A1* | 11/2013 | Kowalkowski | F01N 11/00 |
| | | | 73/114.75 |
| 2013/0311065 A1* | 11/2013 | Sun | F01N 3/2066 |
| | | | 701/104 |
| 2014/0147339 A1* | 5/2014 | Ardanese | B01D 53/9445 |
| | | | 422/119 |
| 2015/0290587 A1* | 10/2015 | Mikami | F01N 3/0814 |
| | | | 422/171 |
| 2015/0315950 A1* | 11/2015 | Hagimoto | F01N 3/023 |
| | | | 73/114.75 |
| 2015/0322837 A1* | 11/2015 | Takada | F01N 3/106 |
| | | | 422/111 |
| 2016/0123945 A1* | 5/2016 | Qi | G01N 33/0037 |
| | | | 73/23.31 |
| 2016/0153814 A1* | 6/2016 | Seimori | G01D 11/245 |
| | | | 73/431 |
| 2016/0169073 A1* | 6/2016 | Chanzy | F01N 3/2066 |
| | | | 60/274 |
| 2016/0356195 A1* | 12/2016 | Hibino | F01N 3/208 |
| 2016/0356196 A1* | 12/2016 | Nakano | F01N 3/208 |
| 2017/0030243 A1* | 2/2017 | Li | F01N 3/208 |
| 2017/0145893 A1* | 5/2017 | Kidokoro | B01D 46/0036 |
| 2018/0113103 A1* | 4/2018 | Okamoto | G01N 31/005 |
| 2018/0142593 A1* | 5/2018 | Wang | B01D 53/9431 |
| 2018/0163589 A1* | 6/2018 | David | F01N 13/0093 |

\* cited by examiner

DETERMINING AN AMMONIA MASS FLOW BETWEEN TWO SCR CATALYTIC CONVERTERS

BACKGROUND OF THE INVENTION

The present invention concerns a method for determining a mass flow of ammonia between two SCR catalytic converters disposed one after the other in an exhaust system. Furthermore, the present invention concerns a computer program that implements each step of the method, as well as a machine-readable memory medium that stores the computer program. Finally, the invention concerns an electronic control unit that is arranged to implement the method.

Selective catalytic reduction (SCR) by means of ammonia or ammonia-releasing reagents represents a promising method for reducing nitrogen oxides in oxygen-rich exhaust gases. The efficiency of a SCR catalytic converter depends on the temperature thereof, on the space velocity of the exhaust gas and very decisively on the level of the ammonia absorbed at the surface thereof. Where absorbed ammonia is also available for the reduction of nitrogen oxides in addition to directly introduced ammonia, the efficiency of the SCR catalytic converter is increased compared to an emptied catalytic converter. The storage behavior depends on the respective operating temperature of the catalytic converter. The lower the temperature, the greater is the storage capacity.

If an SCR catalytic converter has completely filled the storage thereof, then in the event of load steps of an internal combustion engine, the exhaust gases of which are being reduced by means of the SCR catalytic converter, ammonia slip can occur even then if no further ammonia or ammonia-releasing reagents are dispensed into the exhaust system. If the highest possible nitrogen oxide conversions are to be achieved, then it is certainly unavoidable to operate the SCR system with a high level of ammonia. If the temperature of the completely filled SCR catalytic converter then increases because of a load step of the internal combustion engine, then the ammonia storage capacity thereof reduces, which causes ammonia slip.

Said effect is particularly pronounced as a result of the fact that SCR catalytic converters are installed close to the internal combustion engine, so that the SCR catalytic converter rapidly reaches the operating temperature thereof following a cold start of the internal combustion engine. A second SCR catalytic converter downstream of the first SCR catalytic converter can therefore be provided in the exhaust system in order to absorb and then convert ammonia from ammonia slip of the first catalytic converter.

Guidelines for onboard diagnosis (OBD) require that both SCR catalytic converters must be monitored. For this purpose, as a rule a respective nitrogen oxide sensor is provided downstream of both SCR catalytic converters. For cost reasons, usually only one dispensing valve is installed upstream of the first SCR catalytic converter in order to introduce an ammonia-releasing solution of a reduction agent into the exhaust system. Filling the second SCR catalytic converter with ammonia thus takes place only by ammonia slip of the first SCR catalytic converter. The data of said sensors can be used for modeling the level of the two SCR catalytic converters. However, in the event of deviations from the modelled aging of the SCR catalytic converters, the physical levels can deviate significantly from the modelled levels. This can lead to changes in the efficiency of the nitrogen oxide reduction and thereby possibly to exceeding the emission limits.

SUMMARY OF THE INVENTION

The method is used for determining a mass flow of ammonia between two SCR catalytic converters disposed one after the other in an SCR catalytic converter system in an exhaust system, which only comprises one reduction agent dosing unit upstream of the first SCR catalytic converter. The determination is carried out from a signal of a NOx sensor disposed between the two SCR catalytic converters and the signal of a NOx sensor disposed downstream of the second SCR catalytic converter. Here the fact is used that the NOx sensor disposed between the two SCR catalytic converters in such SCR catalytic converter systems reacts cross-sensitively to ammonia in any case, and therefore ammonia from an ammonia slip at the first SCR catalytic converter is also measured in addition to the nitrogen oxides that are not reduced in the first SCR catalytic converter. Using suitable computing methods, the sensor signal of the NOx sensor between the two SCR catalytic converters can be divided into ammonia and nitrogen oxide and thus the mass flow of ammonia can be determined.

In a simple embodiment of the method, a difference between concentration signals provided by the two sensors can be used as the basis for the determination of the mass flow of ammonia. Then a conversion of the concentration to the mass only has to be carried out.

In a more complex embodiment of the method, it is provided that a specific demand for a dosing agent of the SCR catalytic converter system and a specific demand for a dosing agent of the first SCR catalytic converter are calculated from the signal of the NOx sensor disposed between the two SCR catalytic converters and the signal of the NOx sensor disposed downstream of the second SCR catalytic converter. The mass flow of ammonia can then be determined by comparing the integrals against time of the two dosing agent demands. In this case, the area between the two integrals is proportional to the ammonia slip downstream of the first SCR catalytic converter. The specific demand for a dosing agent means here the quotient of the mass of ammonia dispensed into the first SCR catalytic converter and the mass of nitrogen oxides converted in the first SCR catalytic converter or in the entire SCR catalytic converter system. Here the molecular weight of nitrogen dioxide, i.e. 46 g/mol, is always used for the calculation of the converted mass of nitrogen oxides. If the actually dispensed mass of ammonia deviates from the mass of ammonia to be dispensed from the modelling perspective because of controller interventions, then the converted amount of nitrogen oxide must also have been different.

During the calculation of the two dosing agent demands, the mass of ammonia released from a reduction agent that is introduced into the exhaust system by means of the reduction agent dosing unit, and the mass of nitrogen oxides upstream of the first SCR catalytic converter are preferably taken into account. The introduced mass of ammonia can be determined from the actuation of the reduction agent dosing unit. The mass of nitrogen oxides upstream of the first SCR catalytic converter can be determined by means of a NOx sensor installed there or even by means of a model.

In the previously described embodiments of the method, the determination preferably takes place at an operating point of the SCR catalytic converter system at which the respective changes of the levels of ammonia of the two SCR catalytic converters do not exceed a change threshold value. The reliability of the determined mass flow of ammonia is increased if it can be approximately assumed that no ammonia is absorbed and desorbed in the two SCR catalytic converters and thereby contributes to the mass of ammonia flows in the SCR catalytic converter system.

Furthermore, it is preferred in said embodiments of the method that the determination takes place at an operating point of the SCR catalytic converter system at which an ammonia slip at the second SCR catalytic converter does not exceed a slip threshold value. Particularly preferably, said slip threshold value is zero. In principle, SCR•catalytic converter systems are operated with two SCR•catalytic converters so that an ammonia slip downstream of the second SCR catalytic converter is not desirable, because said ammonia would be dissipated into the ambient air. At operating points at which it can be assumed that said target will be achieved, the mass flow of ammonia downstream of the second SCR catalytic converter can be approximately assumed to be zero for the determination of the mass flow of ammonia between the two SCR catalytic converters. If said assumption is not true, the reliability of the determined mass flow of ammonia is degraded.

In a further exemplary embodiment of the method, in which the determination of the mass flow of ammonia is carried out particularly accurately, the efficiency of the second SCR catalytic converter is taken into account during the determination of the mass flow of ammonia. Said efficiency can be obtained from a model.

Modelled levels of ammonia of the two SCR catalytic converters can be corrected by means of the mass flow of ammonia determined according to all embodiments of the method in order to minimize deviations between the physical and modelled levels of ammonia.

The computer program is arranged to perform each step of the method, in particular if it is running on a computer unit or an electronic control unit. It enables the implementation of the method on a conventional electronic control unit without having to make structural changes to the same. For this purpose, it is stored on a machine-readable memory medium. By running the computer program on a conventional electronic control unit, an electronic control unit is produced that is arranged to determine by means of the method a mass flow of ammonia between two SCR catalytic converters disposed one after the other in a SCR catalytic converter system in an exhaust system that only comprises one reduction agent dosing unit downstream of the first SCR catalytic converter.

BRIEF DESCRIPTION OF THE DRAWINGS

Exemplary embodiments of the invention are represented in the drawings and are described in detail in the following description.

DETAILED DESCRIPTION

Figure 1:
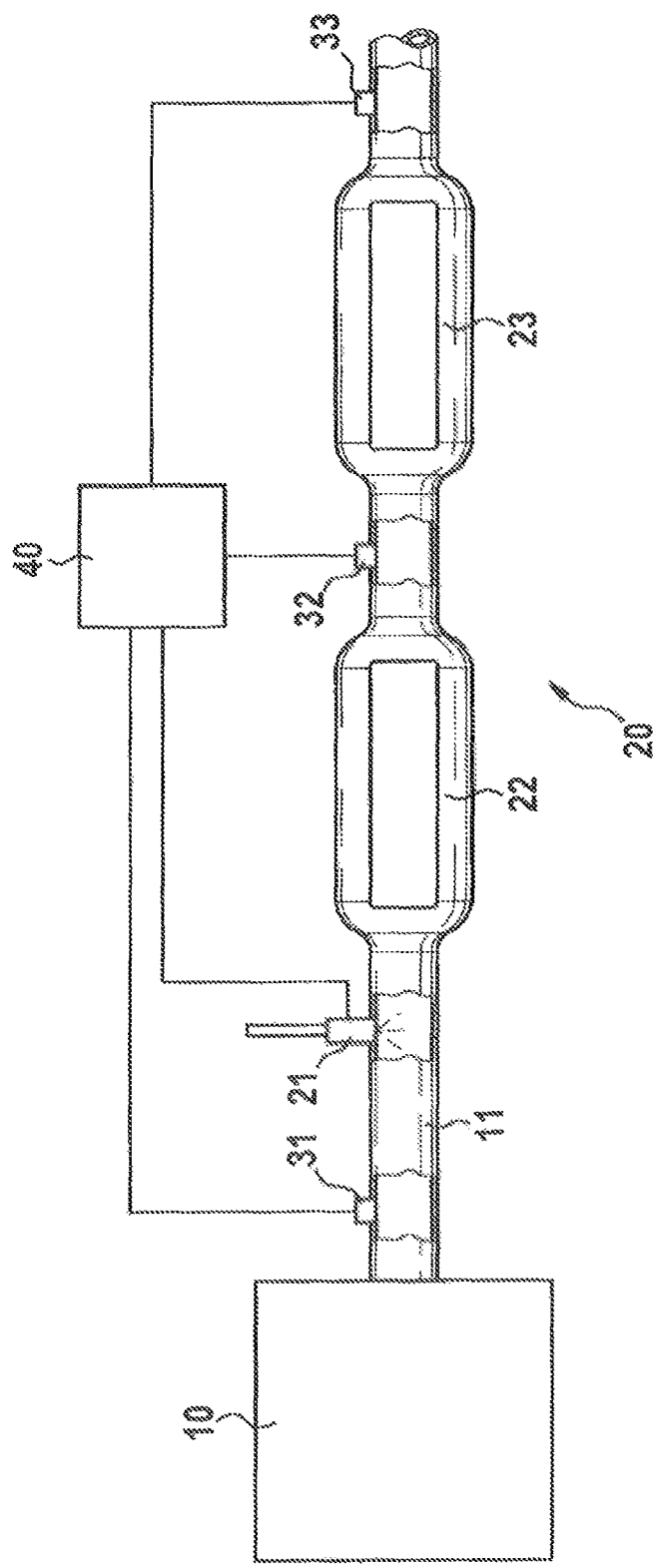
FIG. 1 shows schematically an SCR catalytic converter system with two SCR catalytic converters, the mass flow of ammonia of which between the two SCR catalytic converters can be determined by means of a method according to an exemplary embodiment of the invention.

An internal combustion engine 10 comprises in the exhaust system 11 thereof an SCR•catalytic converter system 20, which is represented in FIG. 1. Said catalytic converter system comprises a reduction agent dosing unit 21, with which a urea water solution can be injected into the exhaust system 11. Ammonia is released from the urea water solution at the high temperatures of the exhaust gas. A first SCR catalytic converter 22 and a second SCR catalytic converter 23 are disposed downstream of the reduction agent dosing unit 21. A first NOx sensor 31 is disposed in the exhaust system 11 upstream of the reduction agent dosing unit 21. A second NOx sensor 32 is disposed between the two SCR catalytic converters 22, 23. A third NOx sensor is disposed downstream of the second SCR catalytic converter 23. All the NOx sensors 31, 32, 33 pass the signals thereof to an electronic control unit 40. As the NOx sensors 31, 32, 33 react cross-sensitively to ammonia, the signals thereof are summation signals for nitrogen oxide and ammonia. The first NOx sensor is, however, disposed upstream of the reduction agent dosing unit 21, so that it measures the amount of nitrogen oxide in the exhaust gas reliably. If the SCR catalytic converter system 20 is operated such that no ammonia slip should occur at the second SCR catalytic converter 23, then it can be assumed that the signal of the third NOx sensor is exclusively based on nitrogen oxides. As an ammonia slip is envisaged at the first SCR catalytic converter 22 in order to supply the second SCR catalytic converter 23 with ammonia, the second NOx sensor certainly always provides a summation signal of ammonia and nitrogen oxides. The reduction agent dosing unit 21 also relays the amount of ammonia dispensed into the exhaust system 11 to the control unit 40.

A first exemplary embodiment of the method according to the invention is based on the knowledge that the difference between the concentration $r(NH_3)\_21$ of the ammonia released from the reduction agent solution introduced by means of the reduction agent dosing unit 21 and the ammonia concentration $r(NH_3)\_32$ at the second NOx sensor 32 corresponds to the difference between the nitrogen oxide concentration $r(NOx)\_31$ upstream of the first SCR catalytic converter 22 and the nitrogen oxide concentration $r(NOx)\_32$ between the two SCR catalytic converters 22, 23 according to equation 1:

$$r(NH_3)\_21 - r(NH_3)\_32 = r(NOx)\_31 - r(NOx)\_32 \quad \text{(Equation 1)}$$

In this case the concentration value $r(sens)\_32$ passed from the second NOx sensor 32 to the control unit 40 corresponds to the sum of the concentrations of nitrogen oxides and ammonia between the two SCR catalytic converters 22, 23 according to equation 2:

$$r(sens)\_32 = r(NOx)\_32 + r(NH_3)\_32 \quad \text{(Equation 2)}$$

Furthermore, according to equation 3 the introduced nitrogen oxide concentration $r(NH_3)\_21$ should correspond to the difference between the nitrogen oxide concentration upstream of the first SCR catalytic converter 22 and the nitrogen oxide concentration $r(NOx)\_33$ downstream of the second SCR catalytic converter 23:

$$r(NH_3)\_21 = r(NOx)\_31 - r(NOx)\_33 \quad \text{(Equation 3)}$$

From equations 1 to 3 equation 4 results, which enables the calculation of the ammonia concentration $r(NH_3)\_32$ between the two SCR catalytic converters 22, 23 from the sensor signals of the second NOx sensor 32 and of the third NOx sensor 33:

$$r(NH_3)\_32 = [r(sens)\_32 - r(NOx)\_33]/2 \quad \text{(Equation 4)}$$

If no ammonia slip takes place at the second SCR catalytic converter 23, then the nitrogen oxide concentration r(NOx)

_33 downstream of the second SCR catalytic converter 23 can be obtained from the signal of the third NOx sensor 33. The mass flow of ammonia can be calculated by determining the two concentration values against time.

In a second exemplary embodiment of the method according to the invention, the specific demand for a dosing agent facDos_22 of the first SCR catalytic converter 22 is calculated according to equation 5. In this case m(NH$_3$)_21 denotes the introduced mass of ammonia and the difference between the mass of nitrogen oxides m(NOx)_31 upstream of the first SCR catalytic converter 22 and the mass of nitrogen oxides m(NOx)_32 downstream of the first SCR catalytic converter corresponds to the mass of nitrogen oxides converted in the first SCR catalytic converter:

$$\text{Dos\_22} = m(NH_3)\_21/[m(NOx)\_31-(m(NOx)\_32+m(NH_3)\_32)] \quad \text{(Equation 5)}$$

The mass of nitrogen oxides m(NOx)_32 and the mass of ammonia m(NH$_3$)_32 cannot be measured directly. Because the mass signal m(sens)_32 provided by the second nitrogen oxide sensor 32 corresponds to the sum of the mass of nitrogen oxides m(NOx)_32 and the mass of ammonia m(NH$_3$)_32 between the two SCR catalytic converters 22, 23, equation 5 can be replaced by equation 6:

$$\text{Dos\_22} = m(NH_3\_21)/[m(NOx)\_31-m(\text{sens})\_32] \quad \text{(Equation 6)}$$

In order to calculate the specific demand for a dosing agent facDos$_{13}$ 20 of the entire SCR catalytic converter system 20, according to equation 7 the mass of nitrogen oxides downstream of the second SCR catalytic converter 22 measured by the third NOx sensor 33 is also necessary:

$$\text{Dos\_20} = m(NH_3\_21/[m(NOx)\_31-m(NOx)\_33] \quad \text{(Equation 7)}$$

Here it is assumed that no ammonia slip takes place downstream of the second SCR catalytic converter 23, so errors are not introduced into the signal of the third NOx sensor 33 by ammonia. Moreover, equation 8 for the entire SCR catalytic converter system 20 can be constructed based on the nitrogen oxide reduction in the first SCR catalytic converter 22:

$$\text{Dos\_20} = [m(NH_3\_21)-m(NH_3\_32)]/[m(NOx)\_31-m(NOx)\_32] \quad \text{(Equation 8)}$$

Figure 2:
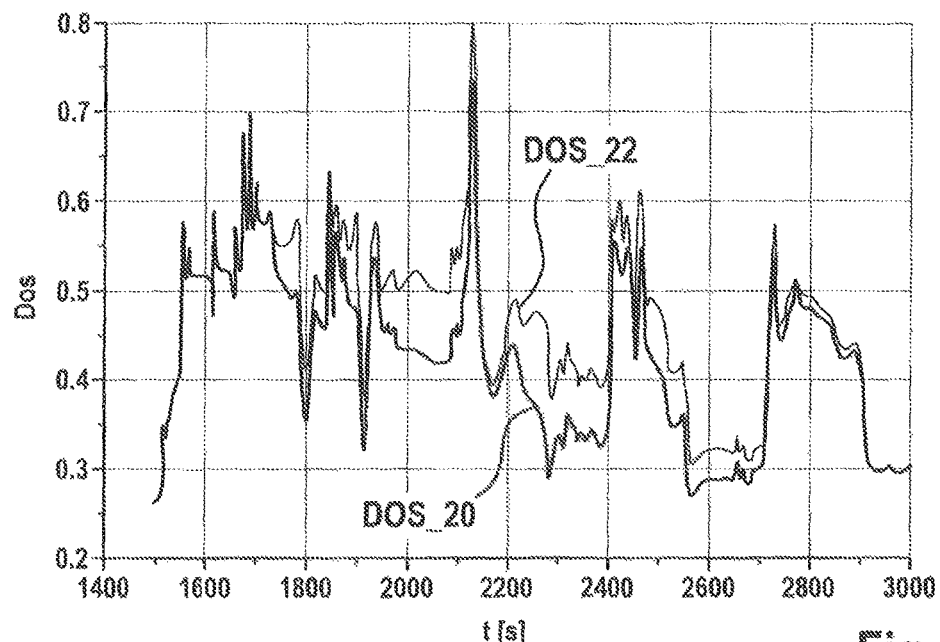
FIG. 2 shows the time profile of the specific dosing agent demand of an SCR catalytic converter system with two SCR catalytic converters and of the specific dosing agent demand of one of said two SCR catalytic converters in a method according to an exemplary embodiment of the invention.
Figure 3:
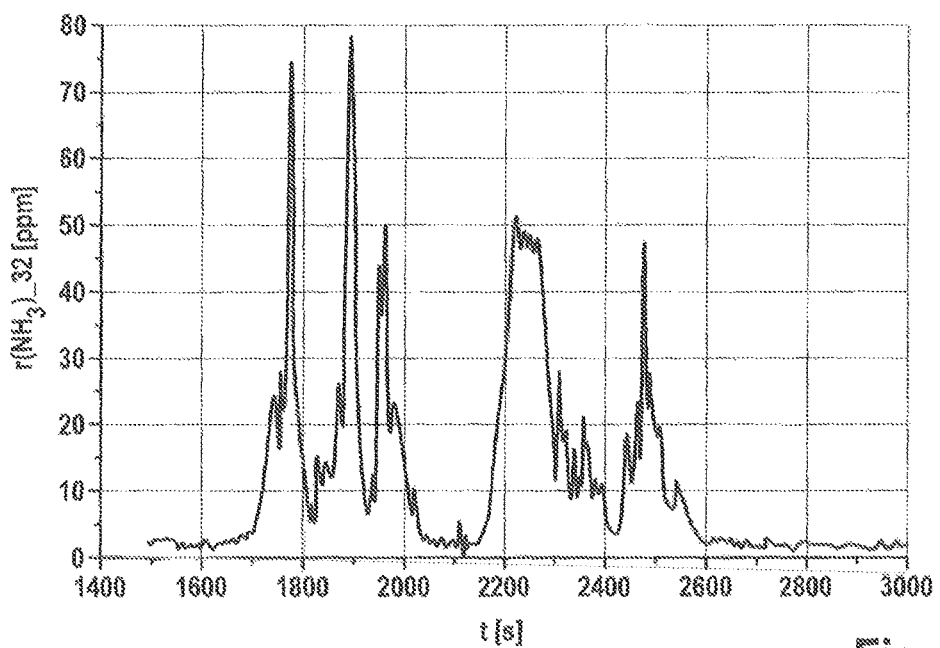
FIG. 3 shows the time profile of the ammonia concentration between two SCR catalytic converters in an exemplary embodiment of the method according to the invention.

By means of equations 6 to 8, the two dosing agent demands facDos_20, facDos_22 can be determined from the available sensor data. Here it must be noted that the molecular weights of ammonia and nitrogen oxides are different. The mass of nitrogen oxides is always calculated using the molecular weight of nitrogen dioxide. The profile thereof against time t in an exemplary operating state of the internal combustion engine 10 is represented in FIG. 2. The difference of the integrals against time of the two dosing agent demands facDos_20, facDos_22 is proportional to the mass flow of ammonia between the two SCR catalytic converters 22, 23. A high mass flow of ammonia, and thereby a large ammonia slip at the first SCR catalytic converter 22, occurs where the profiles against time of the two specific dosing agent demands facDos_20, facDos_22 differ significantly. Where they approximate to each other, the mass flow of ammonia is low. This has been verified by introducing an ammonia sensor that is not shown in FIG. 1 into the exhaust system 11 between the two SCR catalytic converters 22, 23. The profile against time of the ammonia concentration r(NH$_3$)_32 measured by the same is represented in FIG. 3. A calculation of the mass of ammonia m(NH$_3$)_32 from the measured sensor values can be carried out according to equation 9:

$$m(NH_3)\_32 = [(m(NH_3)\_21/\text{facDos}\_20)-(m(NH_3)\_21/\text{facDos}\_22)]/[(1/(\text{facDos}\_20))+1] \quad \text{(Equation 9)}$$

In a third exemplary embodiment of the method according to the invention, the knowledge is used that according to equation 10 the mass flow of nitrogen oxide dm(NOx)_33 downstream of the second SCR catalytic converter 23 corresponds to the difference between the mass flow of nitrogen oxide dm(NOx)_32 between the two SCR catalytic converters 22, 23 and the mass flow of the ammonia slip dm(NH$_3$)_32 of the first SCR catalytic converter 22, to which is added the difference $\Delta$m(NH$_3$) between the mass of ammonia delivered to and the mass of ammonia consumed by the second SCR catalytic converter 23:

$$dm(NOx)\_33 = dm(NOx)\_32 - dm(NH_3)\_32 + \Delta m(NH_3) \quad \text{(Equation 10)}$$

Here too it must be noted that the molecular weights of ammonia and nitrogen oxides are different. Furthermore, the difference $\Delta$m(NH$_3$) corresponds to the mass flow of nitrogen oxide dm(NOx)_32 between the two SCR catalytic converters 22, 23 and the mass flow of nitrogen oxide dm(NOx)_32 between the two SCR catalytic converters 22, 23 multiplied by the efficiency ETA(23) of the second SCR catalytic converter according to equation 11:

$$\Delta m(NH_3) = dm(NO_x)\_32 - ETA(23) \times dm(NOx)\_32 \quad \text{(Equation 11)}$$

The following equation results from the two equations 10 and 11:

$$dm(NOx)\_33 = (1-ETA(23)) \times dm(NOx)\_32 \quad \text{(Equation 12)}$$

Analogous to equation 2, according to equation 13 the mass flow dm(sens)_32 measured by the second NOx sensor corresponds to the sum of the mass flow of nitrogen oxide dm(NOx)_32 and the mass flow of ammonia dm(NH$_3$)_32 between the two SCR catalytic converters:

$$dm(\text{sens})\_32 = dm(NOx)\_32 + dm(NH_3)\_32 \quad \text{(Equation 13)}$$

A possibility results from equations 11 and 12 for calculation of the mass flow of ammonia dm(NH$_3$)_32 according to equation 14:

$$dm(NH_3)\_32 = dm(\text{sens})\_32 \times -[dm(NOx)\_33]/[1-ETA(23)] \quad \text{(Equation 14)}$$

For this purpose, the efficiency ETA(23) can be obtained from a model of the second SCR catalytic converter 23. The mass flow of nitrogen oxide dm(NOx)_33 downstream of the second SCR catalytic converter 23 can be obtained from the sensor signal of the third NOx sensor 33 if no ammonia slip occurs at the second SCR catalytic converter 23.

The invention claimed is:

1. A method for determining a mass flow of ammonia between a first SCR catalytic converter and a second SCR catalytic converter, the second SCR catalytic converter disposed downstream of the first SCR catalytic converter in an SCR catalytic converter system (20) in an exhaust system (11), the exhaust system further comprising a reduction agent dosing unit (21) upstream of the first SCR catalytic converter (22), the method comprising:
    receiving, with an electronic control unit, a first signal from a NOx sensor electrically coupled to the electronic control unit and disposed between the first SCR catalytic converter and the second SCR catalytic converter;
    receiving, with the electronic control unit, a second signal from a second NOx sensor electrically coupled to the electronic control unit disposed downstream of the second SCR catalytic converter; and determining, with the electronic control unit, a mass flow of ammonia between the first SCR catalytic converter and the second SCR catalytic converter.

2. The method according to claim 1, wherein the electronic control unit is configured to determine a difference between the first signal and the second signal when determining the mass flow of ammonia.

3. The method according to claim 1, wherein the determination is carried out at an operating point of the SCR catalytic converter system (20) at which a change of the levels of ammonia of the first SCR catalytic converter and the second SCR catalytic converter does not exceed a change threshold value.

4. The method according to claim 1, wherein the determination is carried out at an operating point of the SCR catalytic converter system (20) at which an ammonia slip at the second SCR catalytic converter (23) does not exceed a slip threshold value.

5. The method according to claim 1, wherein the determination of the mass flow of ammonia is further based upon an efficiency of the second SCR catalytic converter.

6. The method according to claim 1, wherein at least one modelled level of ammonia of the first SCR catalytic converter and the second SCR catalytic converter is corrected based upon the determined mass flow of ammonia.

7. The method according to claim 1, wherein a first specific demand for a first dosing agent for the SCR catalytic converter system and a second specific demand for a second dosing agent for the first SCR catalytic converter are determined by the electronic control unit based upon the first signal and the second signal, and wherein the mass flow of ammonia is determined by comparing an integral against time of the first specific demand and the second specific demand.

8. The method according to claim 7, wherein the determination of the first specific demand and the second specific demand is further based on a second mass of ammonia introduced by the reduction agent dosing unit into the exhaust system and a mass of nitrogen oxides upstream of the first SCR catalytic converter.

9. A non-transitory computer-readable medium storing a program containing instructions that when carried out on an electronic control unit cause the electronic control unit to:
receive a first signal from a first NOx sensor disposed between a first SCR catalytic converter and a second SCR catalytic converter, wherein the second SCR catalytic converter is disposed after the first SCR catalytic converter in an SCR catalytic converter system in an exhaust system;
receive a second signal from a second NOx sensor disposed downstream of the second SCR catalytic converter; and
determine a mass flow of ammonia based upon the first signal and second signal.

10. An electronic control unit (40) that is configured to:
receive a first signal from a first NOx sensor disposed between a first SCR catalytic converter and a second SCR catalytic converter, the second SCR catalytic converter disposed after the first SCR catalytic converter in an SCR catalytic converter system in an exhaust system, wherein the exhaust system further comprises a reduction agent dosing system upstream of the first SCR catalytic converter;
receive a second signal from a second NOx sensor disposed downstream of the second SCR catalytic converter; and
determine a mass flow of ammonia between the first SCR catalytic converter and the second SCR catalytic converter based upon the first signal and the second signal.

* * * * *